United States Patent [19]

Stendel et al.

[11] Patent Number: 4,631,231

[45] Date of Patent: Dec. 23, 1986

[54] PYRETHROID-CONTAINING MOLDED ARTICLES FOR COMBATING ECTOPARASITES

[75] Inventors: Wilhelm Stendel, Wuppertal; Herbert Voege, Leverkusen, both of Fed. Rep. of Germany

[73] Assignee: Bayer Aktiengesellschaft, Leverkusen, Fed. Rep. of Germany

[21] Appl. No.: 646,551

[22] Filed: Aug. 31, 1984

[30] Foreign Application Priority Data

Sep. 17, 1983 [DE]  Fed. Rep. of Germany ....... 3333657

[51] Int. Cl.$^4$ .................... B32B 27/38; B28B 3/20; G09F 3/00
[52] U.S. Cl. .................... 428/413; 428/474.4; 428/480; 428/522; 428/523; 428/500; 428/532; 428/905; 428/907; 264/176 R; 40/301; 128/330; 514/65; 514/920
[58] Field of Search ............... 428/905, 523, 907, 522, 428/500, 480, 413, 474.4, 532; 264/176 R; 40/301; 128/330

[56] References Cited

U.S. PATENT DOCUMENTS

| | | | |
|---|---|---|---|
| 4,037,352 | 7/1977 | Hennart et al. | 428/905 X |
| 4,091,766 | 5/1978 | Colliard | 428/905 X |
| 4,279,213 | 7/1981 | Urahama et al. | 428/907 X |

*Primary Examiner*—P. C. Ives
*Attorney, Agent, or Firm*—Sprung, Horn, Kramer & Woods

[57] ABSTRACT

An article molded of at least one polymer selected from the group consisting of a polyvinyl resin, polyacrylate, epoxy resin, cellulose, cellulose derivative, polyamide and polyester and containing at least one pyrethroid selected from the group consisting of 3'-phenoxy-4'-fluoro-α-cyano-benzyl 2,2-dimethyl-3-(2"-p-chlorophenyl-2"-chlorovinyl)-cyclopropanecarboxylate,3'-phenoxy-4'-fluoro-α-cyano-benzyl 2,2-dimethyl-3-(2",2"-dichlorovinyl)cyclopropane-carboxylate, pentafluorobenzyl permethrate, and isomers thereof. Such articles are especially useful in combating ectoparasites in livestock management, being used in the form of an ear-tag, neck strap, neck strap tag, tail strap, limb strap or halter.

5 Claims, No Drawings

PYRETHROID-CONTAINING MOLDED ARTICLES FOR COMBATING ECTOPARASITES

The invention relates to polyvinyl resin, polyacrylate, epoxy resin, cellulose, polyamide and polyester molded articles which contain pyrethroids, a process for the production of these molded articles, and their use for combating ectoparasites and pests, especially in livestock management.

Molded articles with retarded release of active compound have already been developed for a variety of purposes in combating pests. As a rule, the molded articles are molded of resin-like compositions which contain the active compound, and for combating ectoparasites and pests, especially in livestock management, these are attached, via various application systems, in the form of rings, straps and ear-tags onto the animal to be protected. In addition, the active compounds are frequently introduced into tags which serve the second purpose of identifying animals. Identification tags of this type and their applicators are mentioned in, for example, U.S. Pat. Nos. 3,955,580, 3,916,904, 3,942,480, 3,952,438, 3,952,439, 3,979,847, 3,987,570, 4,000,744, RE 29,536, 4,160,335, 3,357,122, 3,334,434, 3,552,051, 3,675,357, 3,694,949, 3,731,414, 3,867,777, 3,896,572, 3,526,987 and 3,512,289.

Ear-tags impregnated with fenvalerate, chlorpyrifos, stirofos and ronnel for cattle are described in J. ECON. Entomology 71 (5), 764–765, October 1978.

The object of the invention is to improve, in respect of activity and duration of action, the known systems based on the principle described above.

The object is achieved according to the invention by polyvinyl resin, polyacrylate, epoxy resin, cellulose, polyamide and polyester molded articles which contain 3'-phenoxy-4'-fluoro-α-cyanobenzyl 2,2-dimethyl-3-(2''-p-chlorophenyl-2''-chlorovinyl)cyclopropanecarboxylate, 3'-phenoxy-4'-fluoro-α-cyanobenzyl 2,2-dimethyl-3-(2'',2''-dichlorovinyl)cyclopropanecarboxylate and/or pentabenzyl permethrate or their isomeric forms.

The molded articles according to the invention exhibit an action against flies, ticks, mites, fleas and other ectoparasites and pests which is an improvement compared with the state of the art, and they can be employed, preferably, in livestock management, especially in cattle management.

The active compounds according to the invention contain 0.5 to 20% by weight, based on the molded article, of one or more of the abovementioned pyrethroids. The active compound is preferably present in the molded articles in concentrations of 1 to 10% by weight.

Molded articles according to the invention are ear-tags, neck straps, neck strap tags, tail straps, horn straps, limb straps and halters.

Polyvinyl resins, polyacrylates, epoxy resins, cellulose, cellulose derivatives, polyamides and polyesters which are sufficiently compatible with the abovementioned active compounds can be used to produce the molded articles according to the invention. The polymers must possess adequate strength and flexibility in order, when molded to form a strap or an ear tag, not to tear or become brittle. They must have sufficient stability to resist normal wear. In addition, the polymers must permit adequate migration of the active compounds to the surface of the molded article. These properties are fulfilled by, in particular, solid polyvinyl resins, that is to say by polymers which are formed by polymerization of a vinyl double bond.

Examples of typical vinyl resins are polyvinyl halides, such as polyvinyl chloride, polyvinyl chloridevinyl acetate and polyvinyl fluoride; polyacrylate and polymethacrylate esters, such as poly(methyl acrylate) and poly(methyl methacrylate); and polyvinylbenzenes, such as polystyrene and polyvinyltoluene.

Cellulose derivatives include ethers and/or esters thereof, e.g. cellulose acetate, cellulose propionate, cellulose butyrate, cellulose acetate-butyrate, and the like.

To produce the molded articles according to the invention which are based on polyvinyl resin, plasticizers may be used which are customarily used to plasticize solid vinyl resins. The plasticizer used depends on the resin and its compatibility with the plasticizer. Examples of suitable plasticizers are esters of phosphoric acid, such as tricresyl phosphate, esters of phthalic acid, such as dimethyl phthalate and dioctyl phthalate, and esters of adipic acid, such as diisobutyl adipate. It is also possible to use other esters, such as the esters of azelaic acid, maleic acid, ricinoleic acid, myristic acid, palmitic acid, oleic acid, sebacic acid, stearic acid and trimellitic acid, and complex linear polyesters, polymeric plasticizers and epoxidised soy bean oils. The amount of the plasticizer is about 10 to 50% by weight, preferably about 20 to 45% by weight, of the total composition.

The molded articles can also contain other constituents, such as stabilizers, lubricants, fillers and coloring materials, as long as they do not change the fundamental properties of the composition. Suitable stabilizers are antioxidants and agents which protect the molded articles from ultraviolet light and undesired degradation during processing, such as extrusion or molding. Some stabilizers, such as epoxidized soy bean oils, also serve as secondary plasticizers. Examples of lubricants which can be used are stearates, stearic acid and low molecular weight polyethylene. These constituents can be employed in a concentration of up to about 20% by weight of the total composition.

In the production of the molded articles according to the invention which are based on unsaturated acids, the various constituents are mixed dry by known mixing processes and are molded by known extrusion or injection molding processes.

The technical basis for the choice of the process of fabrication for the production of the molded articles according to the invention depends on the rheological properties of the material of the molded article and on the shape of the required article. The processes of fabrication can be adjusted to accord with the fabrication technology or with the type of molding. In respect of fabrication technology, the processes can be divided according to the rheological states passing through them. Accordingly, casting, compression molding, spraying and coating are suitable for viscous materials for molded articles, and injection molding, extrusion, calendering, rolling and, where appropriate, bending are suitable for viscoelastic polymers. Arranged according to the type of molding, the molded articles according to the invention can be produced by casting, dipping, compression molding, injection molding, extrusion, calendering, stamping, bending, deep-drawing, etc.

These processes of fabrication are known and require no further explanation. In principle, the statements made above by way of example for polyvinyl resins apply to polymers such as polyamides and polyesters.

The molded articles according to the invention can be successfully used against numerous injurious parasites (ectoparasites) belonging to the class of arachnida and the class of insecta.

Examples of ectoparasites from the class of arachnida, which are of great importance in tropical, sub tropical and temperate latitudes and which may be mentioned are those from the family of Ixodidae: the Australian and South American one-host cattle tick (*Boophilus microplus*), the African one-host cattle tick (*Boophilus decoloratus*), the multi-host ticks which infest useful and domestic animals, such as *Rhipicephalus appendiculatus, Rhipicephalus evertsi, Amblyomma variegatum, Amblyomma hebraeum, Amblyomma cayennense, Hyalomma truncatum, Dermacentor variabilis* and *Ixodes ricinus,* and from the family of Gamasidae: the red poultry mite (*Dermanyssus gallinae*).

From the family Democidae: the hair follicle mite Demodex spp.; from the family Sarcoptidae:

mites of the genera Sarcoptes and Notoedres, and from the family of Psoroptidae: mites of the genera Psoroptes, Chorioptes and Otodectes.

Examples of ectoparasites from the class of insecta which may be mentioned are:

From the order of Dipteria (Diptera), the following families:

| | |
|---|---|
| Ceratopogonidae with the genus | Culicoides |
| Simuliidae with the genus | Simulium |
| Psychodidae with the genus | Phlebotomus |
| Culicidae with the genera | Culex, Ades, Anopheles |
| Tabanidae with the genera | Tabanus, Haematopota Chrysops, Pangonia |
| Oestridae with the genera | Gastrophilus, Oestrus, Hypoderma, Dermatobia |
| Anthomyidae with the genera | Musca, Stomoxys, Lyperosia, Glossina |
| Tachinidae with the genera | Lucilia, Calliphora, Chrysomys, Phormia, Callitroga, Cordylobi, Booponus |
| Sarcophagae with the genera | Sarcophaga, Wohlfahrtia |
| Hippoboscidae with the genera | Hippobosca, Melophagus, Pseudolynchia |

From the order of Phthiraptera (lice), the following families:

| | |
|---|---|
| Haematopinidae with the genus | Haematopinus |
| Linognathidae with the genera | Linognatus, Solenopotes |
| Pediculidae with the genera | Pediculus, Phthirus |

Furthermore, from the superfamily of Ischnocera, the genera: Damalinia, Trichodectes, Felicola, Columbicola from the superfamily Amblycera, the genera Menopon, Menacanthus and from the order of Siphonaptera (fleas), the genera Ctenocephalides, Ceratophyllus, Pulex, Echidnophaga.

Over the course of time, ticks and flies have become resistant to the phosphoric esters and carbamates which have hitherto been used as control agents, so that in many areas there are increasing doubts about the success of control. To ensure economic livestock management in the infested areas, there is a pressing need for agents with which all stages of development, preferably the adults, can be combated.

The active compounds incorporated in the molded articles according to the invention are known in the form of their isomeric mixtures under the names flumethrin, cyfluthrin and fenfluthrin. The molded articles contain the active compounds as the isomeric mixture of all isomeric components, or in the form of a single isomer or a mixture of two or more isomers.

EXAMPLE

Ear-tag of polyvinyl chloride containing pentafluorobenzyl permethrate (fenfluthrin)

Test on adult flies/*Stomoxys calcitrans, Musca autumnalis*

10 adult flies in each instance (*Stomoxys calcitrans, Musca autumnalis*) are transferred into transparent containers ($20 \times 20 \times 35$ cm) into which a piece (3 cm$^2$) of an ear-tag, containing active compound for cattle, had previously been introduced.

The flies are able to make direct contact with the piece of ear-tag=direct contact, or they are unable to make direct contact with the piece of ear-tag which is covered by a screen=indirect contact.

At specified times after introducing the flies into the containers, the number of irreversibly injured flies (adynamic phase) is determined. The time of onset of these criteria is employed as a measure of the effect.

The superior effect of ear-tags containing fenfluthrin compared with a known compound is clear from the table below.

| Onset of the adynamic phase in adult *Stomoxys calcitrans* and *Musca autumnalis*/hours after introduction of the flies. | | | | |
|---|---|---|---|---|
| | Onset of the adynamic phase/ hours after introduciton of the flies | | | |
| | direct contact | | indirect contact | |
| | *Stomoxys calcitrans* | *Musca autumnalis* | *Stomoxys calcitrans* | *Musca autumnalis* |
| known active compound fenvalerate | 2 | 6 | 6 | 6 |
| petafluorobenzyl permethrate (= fenfluthrin) | 1 | 1 | 2 | 4 |

It will be appreciated that the instant specification and examples are set forth by way of illustration and not limitation, and that various modifications and changes may be made without departing from the spirit and scope of the present invention.

We claim:

1. An article molded of at least one polymer selected from the group consisting of a polyvinyl resin, polyacrylate, epoxy resin, cellulose, cellulose derivative, polyamide and polyester and containing at least one pyrethroid selected from the group consisting of 3'-phenoxy-4'-fluoro-α-cyano-benzyl 2,2-dimethyl-3-(2''-p-chlorophenyl-2''-chlorovinyl)-cyclopropanecarboxylate,3'-phenoxy-4'-fluoro-α-cyano-benzyl 2,2-dimethyl-3-(2'',2''-dichlorovinyl)cyclopropane-carboxylate, pentafluorobenzyl permethrate, and isomers thereof.

2. A molded article according to claim 1, containing the pyrethroid in about 0.5 to 20% by weight.

3. A molded article according to claim 1, containing the pyrethroid in about 1 to 10% by weight.

4. A molded article according to claim 1 in the form of an ear-tag, neck strap, neck strap tag, tail strap, limb strap or halter used in livestock management to combat ectoparasites.

5. An ear-tag according to claim 4, containing pentafluorobenzyl permethrate as the pyrethroid.

* * * * *